United States Patent [19]

van Hardeveld

[11] 4,156,080

[45] May 22, 1979

[54] PROCESS FOR THE PREPARATION OF MELAMINE

[75] Inventor: Rudolf van Hardeveld, Geleen, Netherlands

[73] Assignee: Stamicarbon, B.V., Geleen, Netherlands

[21] Appl. No.: 871,110

[22] Filed: Jan. 19, 1978

[30] Foreign Application Priority Data

Jan. 19, 1977 [NL]  Netherlands .......................... 7700509
Jan. 20, 1977 [NL]  Netherlands .......................... 7700553

[51] Int. Cl.² .......................................... C07D 251/60
[52] U.S. Cl. ................................................. 544/201
[58] Field of Search ......................................... 544/201

[56] References Cited

U.S. PATENT DOCUMENTS

| 3,300,493 | 1/1967 | Hamprecht et al. | 544/201 |
| 3,723,430 | 3/1973 | Kokubo et al. | 544/201 |
| 3,895,007 | 7/1975 | Schwarzmann et al. | 544/201 |

*Primary Examiner*—John M. Ford

*Attorney, Agent, or Firm*—Cushman, Darby & Cushman

[57] ABSTRACT

An improved process for the preparation of melamine from a feed of urea, thermal decomposition products of urea, or a mixture thereof, in the presence of a catalyst and an ammonia-containing gas. The reactor is divided into a lower and an upper reaction zone by a permeable grid or other restriction which reduces the catalyst flow between the two zones to 5 to 75% of what it would have been in the absence of such restriction. The feed is introduced into the lower reaction zone, which is maintained at a temperature of between 325° and 425° C., wherein substantially all of the urea is decomposed into thermal decomposition products, and a major portion of the thermal decomposition products are converted into melamine, which together with the remaining unreacted thermal decomposition products, is passed into the upper reaction zone. In the upper reaction zone, which is maintained at a temperature at least as high as the temperature of the lower reaction zone, substantially all of the remaining unconverted thermal decomposition products are converted into melamine.

15 Claims, 1 Drawing Figure

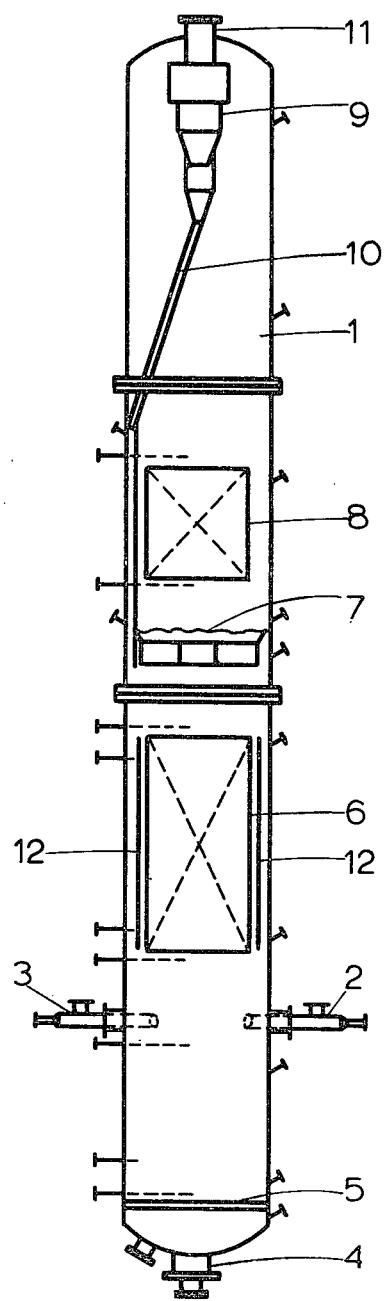

PROCESS FOR THE PREPARATION OF MELAMINE

BACKGROUND OF THE INVENTION

As is commonly known, melamine can be prepared by evaporating liquid or solid urea and introducing the resulting gases, along with a carrier gas, into a fluidized catalyst bed having a temperature of between about 300° and 450° C. It is also known that melamine can be prepared by introducing solid or liquid urea directly into a catalyst bed fluidized with an inert gas and/or ammonia, and having a temperature of between about 300° and 450° C., so that the catalyst particles become loaded with urea. The urea is then thermally decomposed and the resulting decomposition products converted into melamine. The resulting gaseous mixture containing the melamine is then discharged and the melamine is isolated and recovered in a known way.

It has also been proposed to carry out this reaction in a reactor having two separate beds of fluidized granular material. According to U.S. Pat. Nos. 3,158,611, 3,095,416 and 3,152,128, urea is evaporated in a first zone and decomposed in a bed of material that does not promote the conversion of the resulting urea decomposition products into melamine under the reaction conditions. The resulting vapor is then fed into a second zone containing fluidized catalyst, in which zone the conversion into melamine is effected. A variation of such a two-zone process is disclosed in U.S. Pat. No. 3,332,947 wherein, in the first zone, the granular catalyst is loaded with urea and decomposition products thereof at a comparatively low temperature, whereafter this laden catalyst is fed into a second zone maintained at a higher temperature in which the conversion into melamine is effected. However, none of the above known two-zone processes obtain a yield even approaching 95%.

According to Netherlands Patent Application No. 6,503,913, the reaction is effected in a first reaction zone at a temperature of between 370° and 450° C., and in a second reaction zone at a temperature of between 330° and 370° C., and a comparatively small part of the catalyst is periodically or continuously exchanged between the two zones. It is claimed that in this way the activity and selectivity of the catalyst are maintained for a longer period. The yields of such a process are at most 95%.

DESCRIPTION OF THE INVENTION

The primary objective of the present invention is to provide a simple process for preparing melamine in which a high yield and a maximum selectivity can be obtained, and wherein no appreciable corrosion occurs.

A further objective of the invention is to provide such a process which is additionally thermally efficient with respect to the heat of reaction of the exothermic conversion of urea decomposition products to melamine.

According to the invention, melamine is prepared by heating urea, thermal decomposition products of urea, or a mixture thereof in the presence of a catalyst and ammonia or a gaseous mixture containing ammonia, in a reactor containing a fluidized catalyst bed that has been divided into at least two zones separated by a grid, sieve tray or an equivalent member or restriction through which gaseous reactants and products can flow, and which is to some degree pervious to catalyst. The urea or thermal decomposition products are fed into a lower reaction zone, wherein a temperature of between 325° and 425° C. is maintained. Substantially all of the urea is decomposed in such lower reaction zone, and a major portion of the thermal decomposition products are converted into melamine. The resulting melamine containing gas passes into an upper reaction zone, along with catalyst and the remaining unconverted urea decomposition products, through a grid or equivalent pervious restriction which allows a catalyst flow of between about 5 and 75% of what the catalyst flow would be through a similar open area without such restriction. Preferably the amount of undecomposed urea entering the upper zone amounts to not more than 5% of the total amount of urea used. The conversion of urea decomposition products into melamine is substantially completed in the upper reaction zone, which is maintained at a temperature equal to or higher than the temperature in the lower reaction zone.

In this way, it is possible to obtain yields of melamine of over 95% of the theoretical value, and furthermore to approach or to reach the thermodynamic equilibrium by utilizing the reaction heat released by the exothermic conversion of decomposition products into melamine as effectively as possible.

The improved yield obtained in the process according to the invention results from substantially preventing undecomposed urea from entering the upper part of the catalyst bed in the melamine reactor. This effect is achieved by fitting a pervious restriction, such as a grid or an equivalent member, across the reactor so as to divide the catalyst bed into two zones and suppress the axial mixing of the catalyst between the two zones. In this process, the major portion of the melamine is formed in the lower zone. Preferably the conversion into melamine of urea and/or its thermal decomposition products, in the lower bed is at least 60% of the theoretical value. However, the gases flowing from the lower zone still contained a minor amount of decomposition products of urea, and these are converted into melamine in an exothermic reaction in the upper zone which serves as an after-reactor. Owing to the use of a restriction or obstruction that suppresses the axial mixing, but yet permits some exchange of catalyst between the two zones, the heat of reaction released in the upper zone can be absorbed by the catalyst and transferred to the lower zone, where it can be used for the thermal decomposition of urea.

The grid or equivalent restriction must be pervious to the catalyst, so that there is a marked exchange between the two zones, but less than in the case of completely free axial mixing. If there is too much exchange, appreciable amounts of catalyst particles laden with unconverted urea get into the upper zone. If this occurs, the height of the catalyst bed in the upper zone must be made higher in order to obtain a proper yield, thereby diminishing or losing some of the advantage of the invention. On the other hand, if there is very little catalyst exchange, little catalyst heated by the exothermic reaction in the upper zone gets into the lower zone, and part of this heat of reaction is carried out of the reactor along with the reaction gas. However, the improved yield of the invention would be retained in this case.

Therefore, according to the invention, the partition or restriction between the lower and the upper reaction zones should be a grid or an equivalent member that limits the catalyst flow between the zones to between 5 and 75% of the flow that would occur through the same area without such restriction. The resulting average retention time of catalyst in the upper zone is between about 5 and 2000 seconds under the usual reaction conditions.

If a grid or a restriction with a relatively small open area is used, resulting in a relatively low catalyst flow, the heat balance becomes less favorable and a pressure drop occurs. On the other hand, if a grid having a relatively large open area is used, resulting in a high catalyst flow between the two zones, the improvement in yield becomes less significant. Thus, very suitable grids or equivalent restrictions are those that permit a catalyst flow of between about 10 and 50% of the catalyst flow which would result under the same conditions in the absence of such restriction, resulting in a retention time of catalyst in the upper zone of between about 10 and 200 seconds.

As used herein, the term "catalyst flow" is expressed as the amount by weight of catalyst passing through a plane in any direction per unit time per unit surface area.

The partition or restriction between the two zones of the fluidized catalyst bed is preferably a grid with a given free or open area, and may be flat, ribbed or corrogated. It will be apparent that instead of a grid, other types of restrictions suitable for suppressing the axial mixing in the fluidized bed may be used, such as, for example, parallel bars or tubes, cap, baffle or sieve trays or grids of another type. The amount of catalyst exchanged between the lower zone and the upper zone depends not only on the type of grid or equivalent restriction used, but also on the type of catalyst and the gas velocity in the reactor.

The decomposition products of urea are converted to melamine primarily in the lower zone. This lower zone may be constructed and operated in a known and usual way. The retention time of the reactants in this zone may vary within wide limits, but in most cases, it would be between about 5 and 300 seconds.

The temperature in this lower zone is maintained within the desired range by heat exchanging members within the reactor through which a heat transfer agent is circulated, such as molten salt. The temperature in the lower zone, in accordance with the invention, should be maintained between 325° and 425° C., and preferably between 350° and 380° C. The desired temperature within this range depends upon the pressure in the reactor, in that a higher pressure, a higher temperature is preferred.

The feed of urea or urea decomposition products is introduced into the lower zone. Although good results are obtained by injecting molten urea directly into the fluidized bed in the lower zone at any location, variations, such as the introduction of solid urea, or the injection of urea into a series-connected bed of inert material, can also be used with this invention and are not excluded. This results in the production of urea decomposition products which can be fed into the lower zone of the reactor.

The upper zone is designed to be an after-reaction zone, and hence may have a smaller volume than the lower zone. If the reactor has the same diameter in the lower zone as in the upper zone, the height of the catalyst bed in the upper reaction zone may range between 0.2 and 5 meters in the fluidized state. At the lower end of this range, the improvement in yield is only slight, but the improvement in yield is not necessarily proportionately greater with larger amounts of catalyst in the upper zone. Good results are obtained if the height of the catalyst bed in the fluidized state in this upper reaction zone is between about 0.5 and 4.0 meters, and more preferably between about 1.0 and 3 meters.

When the catalyst bed is in a non-fluidized state, the grid or other restriction is situated within the catalyst bed or even slightly over it. When in the fluidized state, the catalyst bed in the lower zone extends to just under the grid or other restriction, and a separate fluidized catalyst bed is present over the grid. The height of the bed over the grid depends on, inter alia, the reactor shape, the open area of the grid, the amount of catalyst, the physical properties of the catalyst and the gas velocity in the reactor. A discussion and formulae with respect to the height of a fluidized bed in an upper zone of a divided fluidized bed reactor can be found in the Canadian Journal of Chemical Engineering 51, pp. 573–577 (1953).

If so desired, suitable members or apparatus for the redistribution of the gas may be fitted within the fluidized catalyst bed in the upper reaction zone.

It is also possible and consistent with the present invention to use a reactor in which the diameter of the upper reaction zone is either larger or smaller than the diameter of the lower reaction zone, although little advantage is obtained with respect to conversion or thermal efficiency as compared to the two zones being of the same diameter.

The average retention time of the reactants in the upper reaction zone depends upon the height of the fluidized bed in this zone and the gas velocity, and generally ranges between about 0.5 and 20 seconds. However, best results are generally obtained with a retention time of reactants in the upper zone of between about 1 and 10 seconds.

The temperature in the upper zone should be at least as high as the temperature in the lower zone, and should generally not exceed about 450° C., and preferably should not exceed about 425° C. A preferred range is from 350° to 380° C.

In a preferred embodiment of the process of the invention the lower reaction zone into which the molten urea is sprayed is itself divided into two vertical zones by one or more vertical partitioning members, which extend from a place in the fluidized bed above the level into which the urea is sprayed up to a level just below the upper surface of the fluidized bed in the lower reaction zone. In at least one of such zones, hereinafter referred to as an ascending zone, the catalyst particles move primarily in an upward or ascending direction. In at least one other of such zones, hereinafter referred to as a descending zone, the catalyst particles move primarily in a downward or descending direction. Heat exchange tubes or members are installed in the ascending zone or zones, and the molten urea is sprayed in or below such ascending zones.

The reaction medium is highly corrosive, particularly in places where unconverted urea is present, and can be especially severe on the higher temperature surface of the heat exchange members. It has already been proposed in Netherlands Patent Application No. 7,305,960, to reduce or avoid this corrosion by introducing the urea into the fluidized bed above the heat exchange members. Such a procedure, however, has the disadvantage that a large amount of catalyst must still be present above the urea feed, and therefore a comparatively larger reactor must be used, and the space velocity of the gas through the reactor must be relatively low in order to avoid complications and to achieve a satisfactory conversion.

When the process is carried out according to this embodiment, the corrosion of the heat exchanger members or tubes is very significantly decreased compared with the corrosion of such tubes in fluidized beds without the vertical partitioning members. This is so even when, in the process of the invention, the urea is introduced at a relatively small distance below the heat exchanger tubes. A significant decrease in corrosion has also been noted in the other metal parts of the reactor, notably the reactor wall and the fluidizing gas distributing plate installed in the bottom of the reactor. Thus, the present invention makes it feasible to use less expensive materials of construction for the reactor wall and the other internal reactor components than was possible under the previously known processes.

The division of the lower fluidized bed into at least two different vertical zones can be realized in various ways. For instance, the lower reaction zone can be divided into two zones by a tubular partitioning member or by a single partition. Division into several zones can also be effected by application of intersecting partitions or by several tubular partitioning members, so that one ascending zone and several descending zones, or a descending zone and several ascending zones are formed. If desired, the vertical partitioning member or members may be so designed that they can additionally function as the heat exchange members.

A preferred vertical partitioning member of the simple construction is a tube of uniform diameter with open upper and lower ends, which is placed within the reactor so as to divide the lower fluidized bed into two concentric zones. The central zone within the partitioning member contains the heat exchange members, and functions as an ascending zone. Such a construction offers the advantage that it is relatively simple to accommodate the heat exchanger in such a central concentric zone, and the rate of corrosion, particularly of the reactor wall, is very significantly reduced since the ascending zone, in which the most corrosive conditions prevail, is enclosed within the tubular partitioning member. The urea spray nozzles should be positioned within the reactor so as to promote the flow of catalyst from the bottom of the descending zone to the bottom of the ascending zone.

Because the vertical partitioning member generally has no bearing function, and the pressure difference between the zones is small, such partitioning member can be of a relatively light construction. The partitioning member can be installed in the reactor in a known way, in either a fixed or detachable position, provided that the flow of the catalyst is not significantly hindered. The partitioning member may, for instance, rest on supports extending from the fluidizing gas distributing plate, be connected to the reactor cover, be attached to the reactor wall by means of connecting pieces, or rest on bosses protruding from the reactor wall. The material of construction for the partitioning member can generally be chosen from materials suitable for the construction of the reactor of the heat exchanging members or tubes, such as various known types of stainless steel.

The lower edge of the partitioning member is located some distance above the place where the urea is sprayed into the fluidized bed. The appropriate distance depends on the positioning of the urea nozzles and the type of urea nozzles used, but in any event should be such that no molten urea is sprayed directly against the partitioning member. Generally, this distance is between about 10 and 100 cm, and preferably between 25 and 60 cm.

The top of the partitioning member extends to a place beneath the upper surface of the lower fluidized bed, so that the catalyst particles can easily get from one vertical zone into the other. The distance between the top of the partitioning member and the upper surface of the lower fluidized bed is at least about 10 cm. The length of this partitioning member should be at least 1 m, so as to insure the advantages of the invention.

The cross-sectional area of the descending zone or zones may, in general, be between 5 and 35% of the total free cross-sectional area of the reactor, and is preferably between 10 and 25% of this total area.

The ratio between the height and the diameter of that portion of the reactor accommodating the catalyst bed divided into several zones in accordance with the invention, may generally lie between 0.5:1 and 10:1, and is preferably between 1:1 and 5:1.

The ratio between the length and the diameter of a tubular partitioning member used in accordance with the invention is preferably between 1:1 and 10:1.

The catalyst bed is maintained in a fluidized state by a fluidizing gas introduced into the bottom of the reactor through a gas distributing element, for instance, a gas distributing plate. If desired, this gas feed may be at a somewhat higher rate under the ascending zone or zones than under the descending zone or zones, in the preferred embodiment.

The urea is introduced directly into the fluidized bed in a molten condition through one or more urea feed nozzles, which are preferably two-phase nozzles. These urea feed nozzles are preferably installed in the wall of the reactor at a location above the gas distributing element, in order to facilitate their installation and maintenance, and to avoid their becoming clogged with catalyst particles in the event the supply of fluidization gas is stopped or reduced. Generally, these nozzles are placed at a location about 10 to 75 cm. above the gas distributing element, in such a way that no molten urea is sprayed directly against the gas distributing element. Preferably, the nozzles are so installed that the "nozzle frame" or spray pattern is directed horizontally or slightly downwards. In the preferred embodiment the positioning of the nozzles should be such that the urea spray promotes the flow of the catalyst particles from the descending or downcomer zone to the ascending or riser zone. The nozzle itself need not be directly under the ascending zone, and the invention may suitably be practiced by spraying urea in such a way that the more concentrated portion of the nozzle flame or spray pattern is under the descending zone, provided that the tip of the nozzle flame extends to a point under the ascending zone.

In addition to the suppression of corrosion, use of the vertical partitioning member in the lower reaction zone promotes mixing in the fluidized bed whereby heat is efficiently transported from the heat exchange means. The combination of the vertical partitioning member and the permeable restriction between the upper and lower reactor zones makes it possible to have a higher urea feed with a yield as high or higher than otherwise possible. The vertical partitioning member, however, should be completely contained in the lower reaction zone and should not extend through the permeable restriction between the upper and lower zones. Otherwise the above advantages of the preferred embodiment would be lost.

Preferably, the upper reaction zone is operated under substantially adiabatic conditions, that is, substantially no heat is added to or removed from the upper reaction zone except that heat contained in the reactants, reaction products, fluidizing and atomizing gas and catalyst. In such case, the temperature in the upper zone is determined by the amount of catalyst exchanged between the upper zone and the isothermally operated lower zone, and by the exothermic reactions that take place in the upper zone. No fresh urea is added to the upper zone. However, it is also possible within the scope of the present invention to remove heat from the upper zone in some other known manner, for example, by means of heat exchangers.

In some instances, it may be desired or necessary to limit the dimensions of the lower reaction zone, which may make it difficult to accommodate sufficient heat transfer surface entirely within the lower zone. In such a case, a comparatively open grid or equivalent restriction may then be used as a partition between the two zones, and part of the total heat transfer surface may be placed in the upper reaction zone. The heat applied in the upper zone will then be absorbed by the catalyst and transferred to the lower zone. This may slightly lower the yield, but it offers the advantage that the total reactor height may be less, and the volume of the catalyst bed in the lower zone may be smaller than need be if the entire heat transfer surface were placed within the lower zone.

The process according to the invention may be carried out at atmospheric pressure or at an elevated pressure of between about 1 and 25 atmospheres absolute, preferably between about 1 and 15 atmospheres absolute, and more preferably at a pressure of between about 5 and 12 atmospheres absolute. The average velocity of the fluidizing gas in the reactor measured over the lower reaction zone may vary between about 5 cm/sec. and 200 cm/sec., but in most cases an average velocity of between about 20 cm/sec. and 70 cm/sec. is preferred.

In practice, the urea is injected as a melt into the reactor by means of a one-phase or two-phase nozzle. If a two-phase nozzle is used, the atomizing gas is preferably the same gas or gaseous mixture that is used as the fluidizing gas.

Ammonia or a gaseous mixture containing ammonia is generally used as the fluidization gas and, if a two-phase urea nozzle is used, as an atomizing gas. The ratio between the ammonia or ammonia containing gas and urea introduced into the reactor may vary between 1 and 5 m$^3$ (N.T.P.) of ammonia per kg., of urea and is preferably between 1.5 and 2 m$^3$ (N.T.P.)/kg.

The catalyst may be any of the well-known catalysts, such as aluminum oxide, (alumina), aluminum oxide on silicon oxide (silica/alumina), silicon oxide (silica), titanium oxide, zirconium oxide, boro phosphate or aluminum phosphate, or a mixture thereof. The term 'catalyst' or 'catalytically active material' here denotes any substance that promotes the conversion of urea into melamine under the reaction conditions.

Generally, a cyclone is installed in the top of the reactor to recover solid catalyst particles from the reaction gases. Such a cyclone is fitted with a stand-pipe for the return of the recovered catalyst particles to the fluidized bed. Under prior art processes, this stand-pipe had to extend into the bottom of the fluidized bed in order to avoid fluidization problems. As a consequence, the cyclone had to be placed relatively high over the bed to overcome the pressure difference resulting from the difference in density between the catalyst particles in the bed and in the vertical tube. However, under the present invention, the lower end of the stand-pipe need only extend into the top of the catalyst bed in a descending zone, resulting in a shorter stand-pipe and making it possible to reduce the overall height of the reactor. The invention will now be explained with reference to the figure, without being restricted thereby.

In the figure, which represents a reactor in which the process of the invention can be realized, the figures have the following references:

1. reactor
2. urea nozzle
3. urea nozzle
4. feed nozzle for fluidizing gas
5. distributing plate for fluidizing gas
6. heat-exchanger tubes
7. sieve tray
8. heat-exchanger tubes
9. de-dusting cyclone
10. standpipe
11. discharge of synthesis gas
12. vertical partitioning member In reactor 1, urea is injected through the nozzles (1, 2), together with NH$_3$, into a fluidized bed of catalyst particles. The bed is fluidized by means of NH$_3$ distributed over the cross-section of the reactor by gas feed nozzle 4 and gas distributing plate 5. The fluidized bed is kept at the desired temperature by means of the heat-exchanger tubes 6, which are here shown diagrammatically.

The heat-exchanger tubes are mounted within a vertical partitioning member (12) of tubular shape.

Reactor 1 is divided into an upper and a lower reaction zone by sieve tray 7, over which heat-exchanger tubes 8 are provided.

In the top of reactor 1 there is a de-dusting cyclone 9, for removing catalyst dust from the reaction gases. The catalyst dust recovered here is returned to the lower catalyst bed through standpipe 10.

The reaction gases leave the reactor through discharge member 11.

EXAMPLE I

The preparation of melamine was carried out in a cylindrical fluid-bed reactor with an internal diameter of 1.45 meters and a total height of 15 meters. The catalyst was fluidized by feeding ammonia through a gas distributing plate equipped with nozzles and was heated by heat-exchanging tubes in the reactor, through which molten salt flowed. Liquid urea was fed to the reactor directly over the gas distributing plate under the heat exchanger by means of two-phase nozzles using ammonia as the atomizing gas. Melamine was isolated from the reactor products leaving the reactor in a known way. At 6 meters over the gas distributing plate, a sieve tray with an open area of 40% was fitted in the reactor so that the catalyst flow was reduced to about 10% of what the catalyst flow would have been without the sieve tray. With 5800 kg of catalyst in the reactor, the height of the catalyst bed in a fluidized state was measured at 1.7 meters in the upper reaction zone, or after-reactor, over the sieve tray. The two-phase nozzles fed in 644 grams of urea per second with 405 grams of ammonia per second as the atomizing gas. Ammonia was used as the fluidization gas and was fed at a rate of 401 grams per second, so that the ammonia/urea ratio was 1.8 m$^3$ (N.T.P.)/kg. of urea. The relationship between the urea feed and catalyst present in the reactor was such that 0.40 kg. of urea per hour was fed per kg. of catalyst. The reaction was carried out in the reactor which was at an absolute pressure of 6.5 atm., and a maximum temperature of 390° C. was measured in the upper reaction zone. As a result of the exothermic reactions in the adiabatically operated upper reaction zone, the temperature in this upper reaction zone was 1.5° C. higher than the temperature in the lower zone. The yield of the conversion of the anhydrous urea into melamine amounted to 98.7% of the theoretical value.

EXAMPLE II

A series of experiments A-F were carried out in the reactor described in Example I and several variables were changed as shown in the Table below. Experiments G and H were also carried out in this reactor, except a heat exchanger was additionally placed in the catalyst bed in the upper reaction zone above the sieve tray that supplied about 25% of the total heat fed to the reactor. The relatively small rise in the temperature difference between the catalyst beds in the upper and lower zones in experiments G and H indicates effective transport of catalyst, and hence heat, between the two catalyst beds. The results of these experiments are compiled in the following Table.

reactor was 6.5 atm and the temperature was maintained at 385° C.

Under these conditions the efficiency of the conversion of anhydrous urea into melamine was 97.5% of the theoretical value.

After an operating period of 6 months, during which the urea supply was varied between approximately 300 and 950 g/s and the ammonia/urea ratio was varied between 1.4 and 3.4 m$^3$ (N.T.P.) of NH$_3$/kg of urea, the reactor was stopped and emptied. Upon inspection, no measurable corrosion was observed in the form of reduction of the wall thickness or pitting of the heat-exchanger tubes or other metal parts of the reactor, which were made of CrNi (18-9) steel. This means that the corrosion rate was less than 0.1 mm/year.

But corrosion in the form of pitting of the tubes made of CrNi (18-9) steel was observed after an equivalent operating period of 6 months in a conventional fluid-bed reactor without vertical partitions, in which the distance between the urea nozzles and the superimposed heat-exchanger tubes is 0.20 m.

In the process according to the invention urea was sprayed by means of a few nozzles with a nozzle flame length of between 0.7 and 1.0 m. In the conventional reactor several hundred urea nozzles were used with a flame length of 0.2 m, so that the ratio between the flame length and the distance to the heat exchanger tubes was approximately the same in both cases.

What is claimed is:

TABLE

| Experiment | Urea g/sec. | Atomization Ammonia g/sec. | Fluidization Ammonia g/sec. | NH$_3$/Urea m$^3$(NTP)/kg | Catalyst kg | Height of bed in upper zone m | P atm abs | T upper zone °C. | ΔT lower/upper °C. | yield % | retention time of catalyst upper zone sec. |
|---|---|---|---|---|---|---|---|---|---|---|---|
| A | 660 | 390 | 476 | 1.7 | 5600 | 0.5 | 6.4 | 390 | 7 | 96 | 9 |
| B | 660 | 395 | 480 | 1.7 | 6100 | 1.0 | 6.3 | 390 | 5 | 99.5 | 20 |
| C | 660 | 400 | 470 | 1.7 | 6800 | 2.0 | 6.5 | 391 | 6 | 99.5 | 40 |
| D | 665 | 400 | 466 | 1.7 | 7400 | 2.7 | 6.4 | 391 | 3.5 | 99.0 | 54 |
| E | 650 | 352 | 571 | 1.9 | 6800 | 1.6 | 6.4 | 380 | 4 | 97.5 | 31 |
| F | 652 | 395 | 535 | 1.9 | 7000 | 1.6 | 6.4 | 401 | 6 | 98.9 | 31 |
| G | 640 | 400 | 330 | 1.5 | 7800 | 3.0 | 6.4 | 390 | 7 | 99.0 | 55 |
| H | 760 | 400 | 420 | 1.4 | 7000 | 1.8 | 6.5 | 390 | 10 | 99.3 | 34 |

EXAMPLE III

A tube having a diameter of 1.30 m and a length of 5.20 was installed concentrically in a cylindrical fluid-bed reactor provided at the bottom with a gas-distributing plate, through which ammonia is fed as the fluidization gas. The internal diameter of the reactor amounted to 1.45 m. Two-phase nozzles for spraying urea were installed in the reactor wall 0.20 m above the gas-distributing plate and 0.40 m below the lower edge of the tube. Under operating conditions, the flame or spray pattern of the nozzles extended to a point under the lower opening of the tube. The tube also enclosed the bundles of heat-exchange tubes for the supply of heat. The lowest heat-exchange tubes were positioned 0.80 m above the urea nozzles. At a distance of 6.60 m above the gas-distributing plate a screening plate having an open area of 40% was mounted in the reactor. The reactor was filled with 6000 kg. of silica-alumina catalyst, which is sufficient to reach a bed height of 9.0 meters over the gas distributing plate when fluidized under operating conditions. Urea was fed in at the rate of 940 g of urea per second, with 200 g of ammonia per second as atomizing gas and 1000 g of ammonia per second as fluidization gas. The absolute pressure in the 1. In a process for the preparation of melamine by heating a feed selected from the group consisting of urea, thermal decomposition products of urea, or mixtures thereof in the presence of a catalyst and an ammonia-containing gas in a reactor divided into at least two reaction zones, the improvement wherein said reactor is divided into a lower reaction zone and an upper reaction zone separated by a pervious restriction which limits the flow of catalyst between said lower and upper reaction zones to between about 5 and 75% of such catalyst flow which would occur in the absence of such restriction, said feed being introduced into said lower reaction zone, and a melamine-containing gas being removed from said upper reaction zone, and wherein:

said lower reaction zone has heating means and is maintained at a temperature of between 325° and 425° C. whereby the urea portion of the feed introduced therein is substantially decomposed, by application of heat, into thermal decomposition products of urea, and a major portion of the thermal decomposition products of urea present in said lower reaction zone is converted into melamine which, together with the remaining unconverted thermal decomposition products, is passed into said upper reaction zone; and said upper reaction zone is maintained at a temperature at least as high as the temperature in said lower reaction zone whereby substantially all of said remaining unconverted thermal decomposition products are converted into melamine.

2. The process of claim 1, wherein said pervious restriction limits the flow of catalyst between said lower and upper reaction zones to between 10 and 50% of such catalyst flow which would occur in the absence of such restriction.

3. The process of claim 1, wherein the temperature in the upper reaction zone is higher than the temperature in the lower reaction zone.

4. The process of claim 1, wherein the reaction in the upper reaction zone is carried out under substantially adiabatic conditions.

5. The process of claim 1, wherein the average retention time of said remaining unconverted thermal decomposition products in the upper zone is between 0.5 and 20 seconds.

6. The process of claim 1, wherein the average retention time of said remaining unconverted thermal decomposition products in the upper zone is between 1 and 10 seconds.

7. The process of claim 1, wherein said urea is sprayed in a molten form directly into said lower reaction zone, wherein said lower reaction zone is divided into at least two zones by at least one vertical partitioning member, extending from a point in said fluidized bed above the level into which said urea is sprayed to a point just below the upper surface of said lower reaction zone, and wherein, in at least one such zone, said catalyst particles moves primarily in an ascending direction, and in at least one other such zone said catalyst particles move primarily in a descending direction, said heating means being located within said at least one ascending zone and said urea being sprayed into said fluidized bed in a manner so as to move said catalyst particles from said at least one descending zone to said at least one ascending zone.

8. The process of claim 7, wherein the cross-sectional area of said at least one descending zone ranges between 5 and 35% of the total free cross-sectional area of the reactor.

9. The process of claim 7, wherein the cross-sectional area of said at least one descending zone ranges between 10 and 25% of the total free cross-sectional area of the reactor.

10. The process of claim 7, wherein said reactor is substantially cylindrical and said partitioning member is a tubular member of substantially uniform diameter fitted concentrically in said reactor.

11. The process of claim 7, wherein the fluidized bed within said tubular member functions as said at least one ascending zone.

12. The process of claim 7, wherein the length of said tubular member is between 1 and 10 times the diameter of said tubular member.

13. The process of claim 7, wherein a cyclone for the recovery of catalyst particles from reaction gases leaving said reactor is mounted in the top of said reactor, said cyclone having a stand-pipe through which recovered catalyst particles are returned to said lower reaction zone, the lower end of such stand-pipe ending in the top portion of said at least one descending zone in said lower reaction zone.

14. The process of claim 1, wherein the temperature in said lower reaction zone is within the range of between 325° and 380° C., and the temperature in said upper reaction zone is in the range between 350° and 400° C.

15. The process of claim 1, wherein the absolute pressure in said reactor is between 5 and 12 atmospheres absolute.

* * * * *